United States Patent [19]

Langlois et al.

[11] Patent Number: 4,897,409
[45] Date of Patent: Jan. 30, 1990

[54] 5-AMINOETHYLOXAZOLIDIN-2-ONE DERIVATIVES

[75] Inventors: Michel Langlois, Buc; Alain-René Schoofs, Paris; Jean-François Rumigny, Rueil Malmaison; Philippe Dostert; Margherita Strolin-Benedetti, both of Paris; Patrice Renaut, Fontaine Les Dijon, all of France

[73] Assignee: Delalande S.A., Courbevoie, France

[21] Appl. No.: 92,126

[22] Filed: Sep. 2, 1987

[30] Foreign Application Priority Data

Sep. 3, 1986 [FR] France .................. 86 12369
Dec. 30, 1986 [FR] France .................. 86 18368

[51] Int. Cl.$^4$ .................. A61K 31/42; C07D 263/22
[52] U.S. Cl. .................. 514/376; 548/229; 548/232
[58] Field of Search .................. 548/229, 232; 514/376

[56] References Cited

U.S. PATENT DOCUMENTS

| 4,435,415 | 3/1984 | Bourgery et al. | 548/229 |
| 4,476,136 | 10/1984 | Dostert et al. | 548/229 |
| 4,598,084 | 7/1986 | Strolin-Benedetti et al. | 548/229 |

FOREIGN PATENT DOCUMENTS

| 259228 | 3/1988 | European Pat. Off. | 548/229 |
| 2500450 | 8/1982 | France | 548/229 |
| 2076813 | 12/1981 | United Kingdom | 548/229 |

Primary Examiner—Mukund J. Shah
Assistant Examiner—Cecilia Shen
Attorney, Agent, or Firm—Finnegan, Henderson, Farabow, Garrett & Dunner

[57] ABSTRACT

A mixture of the 4 stereoisomers of formula (I) below, each of the pairs of corresponding racemic diastereoisomers and each of the enantiomers corresponding to each pair, that is to say each of said stereoisomers:

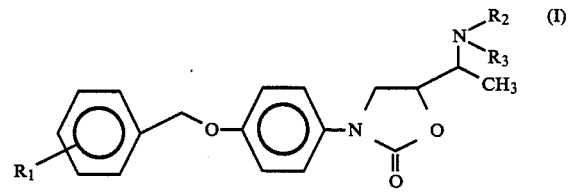

in which $R_1$ represents:
a hydrogen atom,
an alkoxy group comprising from 1 to 4 carbon atoms,
a trifluoromethyl group, or
one or two halogen atoms;

and the pair ($R_2$, $R_3$) has one of the following meanings: (H, H), (H, $C_1$–$C_4$ alkyl), ($C_1$–$C_4$ alkyl, $C_1$–$C_4$ alkyl), as well as their organic and inorganic acid addition salts.

The compounds of formula (I) are therapeutically useful.

6 Claims, No Drawings

5-AMINOETHYLOXAZOLIDIN-2-ONE DERIVATIVES

The present invention relates to new oxazolidin-2-ones, a process for the preparation thereof and their therapeutic use.

The oxazolidin-2-ones according to the invention correspond more precisely to the formula:

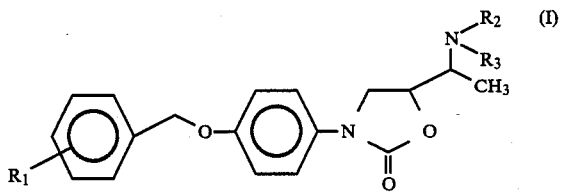

in which $R_1$ represents:
a hydrogen atom,
an alkoxy group comprising from 1 to 4 carbon atoms, more particularly a methoxy group in the meta position,
a trifluoromethyl group, more particularly in the meta or para position, or
one or two halogen atoms, more particularly in the meta and/or para position;
and the pair ($R_2$, $R_3$) has one of the following meanings: (H, H), (H, $C_1$-$C_4$ alkyl), ($C_1$-$C_4$ alkyl, $C_1$-$C_4$ alkyl).

The present invention also extends to the inorganic or organic acid addition salts of these oxazolidin-2-ones.

As a result of the above compounds (I) comprising two asymmetric carbon atoms in their molecules, each exists in the form of a mixture of 4 stereoisomers symbolized below by IA(+), IA(−), IB(+), and IB(−), the symbol A corresponding to the erythro relative configuration and B to the threo relative configuration. This mixture can be separated into two pairs of racemic diastereoisomers, namely the erythro pair IA(+), IA(−) and the threo pair IB(+), IB(−), which can also be symbolized by IA(±) and IB(±), each pair itself being capable of being resolved to isolate the corresponding enantiomers.

The present invention thus covers each of the mixtures of 4 stereoisomers of formula (I), each of the pairs of corresponding racemic diastereoisomers and each of the enantiomers corresponding to each pair, that is to say each of said stereoisomers.

The process according to the invention for preparing the compounds of formula (I) is as follows:

In a first stage, the anilines of formula:

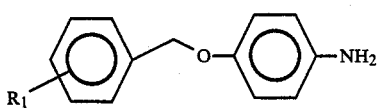

are condensed, $R_1$ having the same meaning as in formula (I), respectively with the mixture of the 4 stereoisomers of 1,2-epoxy butan-3-ol of formula:

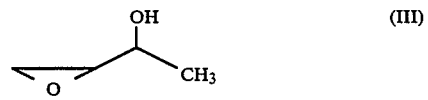

this condensation preferably being effected under heat in an organic solvent, in particular under reflux in an organic hydroxylated solvent such as isopropanol.

The mixture of the 4 stereoisomers of formula (III) is itself obtained by epoxidation of the racemic but-3,4-ene-2-ol of formula:

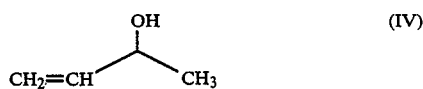

To effect this epoxidation, use is made of an epoxidation agent such as meta-chloroperoxybenzoic acid and the operation is preferably carried out at ambient temperature in an organic solvent such as methylene chloride.

In a second stage, each mixture of 4 stereoisomers of formula (V), obtained in the first stage:

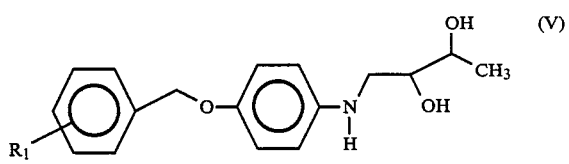

where $R_1$ has the same meaning as in formula (I), is subjected to cyclization by the action of ethyl carbonate in the presence of sodium ethoxide, preferably under heat in an organic solvent, particularly under reflux in toluene, which leads to a mixture of 4 stereoisomers of formula:

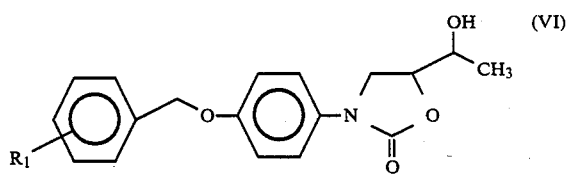

where $R_1$ has the same meaning as in formula (I).

In a third stage, each mixture of 4 stereoisomers of formula (VI) is subjected to silica column chromotography under medium pressure, which allows said mixture to be separated into two pairs of racemic diastereoisomers, namely a pair (the less polar) of erythro relative configuration VI A(+)/VI A(−) [or VI A(±)] and a pair (the more polar) of threo relative configuration VI B(+)/VI B(−) [or VI B(±)].

In a fourth stage, each pair VI A(±) and VI B(±) is resolved to isolate the corresponding enantiomers.

The resolution of the erythro pair VI A(±) can, for example, be effected by esterification with the aid of phenoxy-2-propanoyl chloride (+) (VII) in pyridine, according to the following scheme:

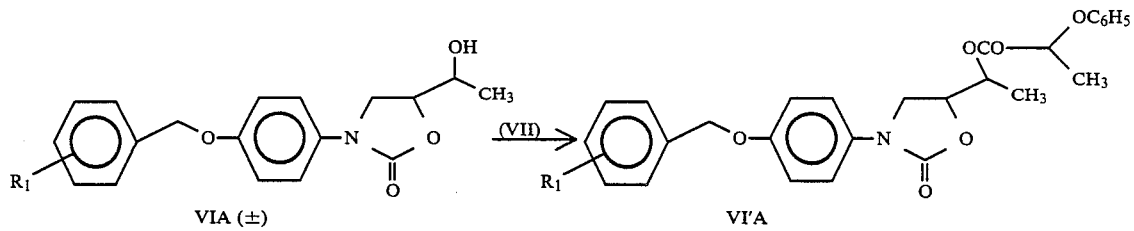

VIA (±)  →(VII)  VI'A this esterification being followed by separation by silica column chromatography under medium pressure of the pair of erythro diastereoisomers VI' A, which leads on the one hand to the less polar ester enantiomer VI' A(+) and on the other hand to the more polar ester enantiomer VI' A(−). The two ester enantiomers VI' A(+) and VI' A(−) thus isolated are then saponified, for example in NaOH, to obtain, respectively, the enantiomer VI A(+) and the enantiomer VI A(−).

Resolution of the threo pair VI B(±) can be effected by esterification with the aid of α-methoxy α-trifluoromethylphenylacetyl chloride (−) (VIII) in pyridine according to the scheme:

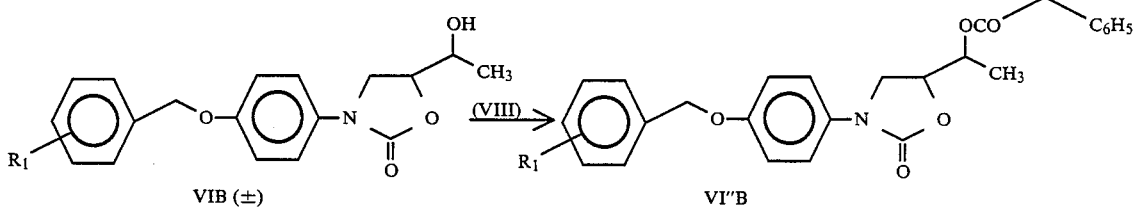

VIB (±)  →(VIII)  VI"B this esterification being followed by separation by silica column chromatography under medium pressure of the pair of threo diastereoisomers VI" B, which leads on the one hand to the less polar ester enantiomer VI" B(+) and on the other hand to the more polar ester enantiomer VI" B(−). The two ester enantiomers VI" B(+) and VI" B(−) thus isolated are then saponified, for example in NaOH, to obtain, respectively, the enantiomer VI B(+) and the enantiomer VI B(−).

Furthermore, it should clarified at this point that the absolute configuration of each of the enantiomers VI A(+), VI A(−), VI B(+) and VI B(−) was determined by the method of partial kinetic resolution of α-phenylbutyric anhydride by these enantiomers (R. Weidmann, A. R. Schoofs and A. Horeau, Comptes Rendus Acad. Sci., Paris, Series II, 1984, page 319 and references cited). Thus:

to the enantiomer VI A(+) was attributed the absolute configuration (S, R),
to the enantiomer VI A(−) was attributed the absolute configuration (R, S),
to the enantiomer VI B(+) was attributed the absolute configuration (S, S), and
to the enantiomer VI B(−) was attributed the absolute configuration (R, R).

In a fifth stage, there are formed respectively the mesylate of the stereoisomers VI A(+), VI A(−), VI B(+) and VI B(−), in particular by reaction of a mesyl halide with these stereoisomers, the resultant mesylates corresponding to the formula:

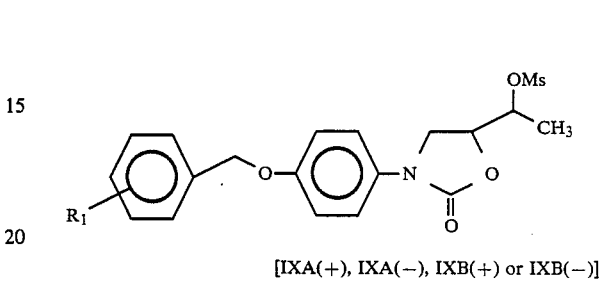

[IXA(+), IXA(−), IXB(+) or IXB(−)]

where $R_1$ has the same meaning as in formula (I) and Ms is the mesyl group, this reaction being effected in the presence of an organic base such as triethylamine, preferably in an organic solvent, in particular a halogenated organic solvent such as methylene chloride.

In the sixth and last stage, each mesylate stereoisomer obtained in the preceding stage is caused to react, optionally in the presence of an organic solvent and in particular a hydroxylated organic solvent such as ethanol or isopropanol, with a compound of the formula:

where the pair ($R_2$, $R_3$) has the same meaning as in formula (I), which leads to the stereoisomer corresponding to formula (I). It should be noted that the nucleophilic substitution by the compound (X) occurs with inversion of configuration. More precisely:

from the mesylate stereoisomer IX A(+) of absolute configuration (S, R), the threo stereoisomer (+) [I B(+)] of absolute configuration (S, S) is obtained,
from the mesylate stereoisomer IX A(−) of absolute configuration (R, S), the threo stereoisomer (−) [I B(−)] of absolute configuration (R, R) is obtained,
from the mesylate stereoisomer IX B(+) of absolute configuration (S, S), the erythro stereoisomer (+) [I A(+)] of absolute configuration (S, R) is obtained, and
from the mesylate stereoisomer IX B(−) of absolute configuration (R, R), the erythro stereoisomer (−) [I A(−)] of absolute configuration (R, S) is obtained.

In a variation the compounds of formula (I) can be prepared in the following way.

The above-defined first four stages are repeated, using, by way of the starting product, the compound of formula:

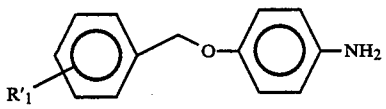
(IIa)

where R'₁ represents only one of the meanings given for R₁ in formula (I), which leads to the 4 stereoisomers of formula:

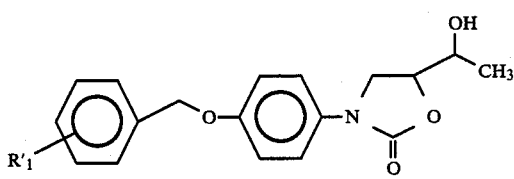

VIaA(+) (S,R)
VIaA(−) (R,S)
VIaB(+) (S,S)
VIaB(−) (R,R)

where R'₁ has the same meaning as in formula (IIa).

These 4 stereoisomers are then:
either treated respectively as in the above-described fifth and sixth stages, which leads to the 4 stereoisomers of formula:

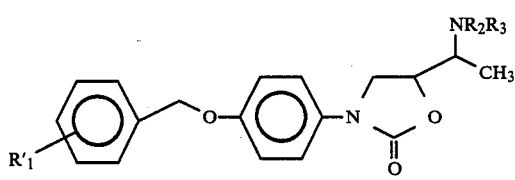

IaB(+) (S,S)
IaB(−) (R,R)
IaA(+) (S,R)
IaA(−) (R,S)

where R'₁ has the single meaning given for formula (IIa) and the pair R₂, R₃ has the same meanings as in formula (I),
or subjected respectively to debenzylation, which leads to the 4 stereoisomers of formula:

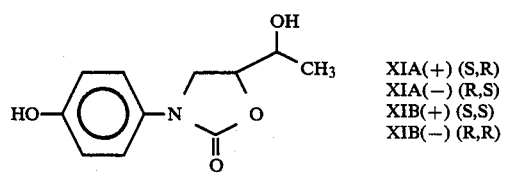

XIA(+) (S,R)
XIA(−) (R,S)
XIB(+) (S,S)
XIB(−) (R,R)

This debenzylation can, in particular, consist in hydrogenolysis in the presence of a hydrogenolysis catalyst such as palladium on carbon, preferably in an organic solvent such as a hydroxylated organic solvent like ethanol, under a hydrogen atmosphere.

This debenzylation is followed by alkylation of the phenolic function of the stereoisomers XI A(+) (S, R), XI A(−) (R, S), XI B(+) (S,S) and XI B(−) R, R), by a compound of formula:

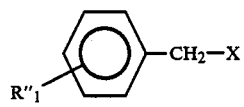
(XII)

where R"₁ has the same meanings as R₁ in formula (I), except the meaning of R'₁ given for formula (IIa) and X is a good leaving group such as a halogen atom. This alkylation is preferably effected in an organic solvent, in particular a polar organic solvent such as acetonitrile, dimethylformamide, dimethylsulfoxide or butan-2-one, in the presence of an inorganic base, particularly potassium carbonate.

From this alkylation there result, respectively, the four stereoisomers of formula:

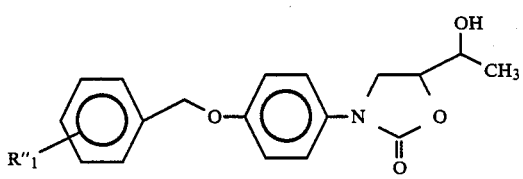

XIIIA(+) (S,R)
XIIIA(−) (R,S)
XIIIB(+) (S,S)
XIIIB(−) (R,R)

where R"₁ has the same meanings as in formula (XII).

These last 4 stereoisomers are then treated respectively as in the previously described fifth and sixth stages, which leads to the 4 stereoisomers of formula:

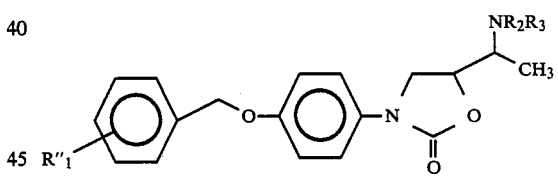

IbB(+) (S,S)
IbB(−) (R,R)
IbA(+) (S,R)
IbA(−) (R,S)

where R"₁ has the same meanings as in formula (XII) and the pair (R₂, R₃) has the same meanings as in formula (I).

It should be noted that in the above and in the following, when the absolute configuration of the compounds according to the invention is symbolized by (S, R), this means that the asymmetric carbon of the oxazolidinone ring has the configuration S and the other asymmetric carbon the configuration R. In the same way, when the absolute configuration of the compounds according to the invention is symbolized by (R, S), this means that the asymmetric carbon of the oxazolidinone ring has the configuration R and the other asymmetric carbon has the configuration S.

The following preparations are given by way of example to illustrate the invention.

EXAMPLE 1

Synthesis of a mixture of four 1,2-epoxybutan-3-ol stereoisomers [III] (code number 790255)

A solution of 33.3 g (0.46 mol) of but-3,4-ene-2-ol in 100 ml of $CH_2Cl_2$ is added drop by drop to a solution cooled to 0° C. of 83.6 g (0.48 mol) of metachloroperoxybenzoic acid in 250 ml of $CH_2Cl_2$. After 20 hours agitation at 20° C., the partially gelled medium is cooled to −18° C. and then filtered. The organic phase is stirred for 30' in the presence of 10 g of solid $Na_2CO_3$. After filtration and evaporation under a very slight vacuum, 36 g of a light yellow oil (yield: 88%) is recovered, corresponding to the expected mixture and comprising 65% threo isomer and 35% erythro isomer.

EXAMPLE 2

Synthesis of a mixture of four 1-[4-(3-chlorobenzyloxy)phenylamino] butane-2,3-diol stereoisomers [V] (code number 340245)

A solution containing 50 g (0.21 mol) of 4-(3'-chlorobenzyloxy) aniline and 21.6 g (0.24 mol) of the mixture obtained in Example 1 in 850 ml of isopropanol is refluxed for 6 hrs 30 mins. When the isopropanol has evaporated, the crude mixture is purified by flash silica chromatography (eluant: $CH_2Cl_2$—$CH_3OH$: 97-3). 34 g (yield: 49%) of white solid is recovered, corresponding to the product expected and having a melting point of from 95°–96° C.

EXAMPLE 3

Preparation of a mixture of four 3-[4-(3-chlorobenzyloxy) phenyl] 5-(1-hydroxyethyl) oxazolidin-2-one stereoisomers [VI]

From a solution of 600 ml of toluene containing 33.4 g (0.10 mol) of the mixture obtained in Example 2, 150 ml of solvent is distilled in an argon atmosphere. Then, successively, 15 g (15.5 ml; 0.127 mol) of ethyl carbonate and 3.4 ml of a solution of EtONa in 1M anhydrous EtOH are added. After 4 hrs 30 mins of reflux, the cyclization reaction is complete. The reaction medium is concentrated, then taken up by 300 ml of methyl ethyl ketone. After washing with 2N HCl, then with a saturated NaCl solution, 35 g of brown solid is recovered corresponding to the product expected.

EXAMPLE 4

Separation of the two pairs of racemic diastereoisomers [VIA(±) and VIB(±)] of 3-[4-(3-chlorobenzyloxy). phenyl] 5-(1-hydroxyethyl) oxazolidin-2-one [VI]

The mixture obtained in Example 3 is subjected to chromatography under medium pressure (eluant:ethyl acetate-heptane: 70-30) and 2 products of different mobility on an $SiO_2$ plate are isolated:
the more mobile product (the less polar)—11.4 g of a white solid with a melting point of 88° C.—consisting of the racemic diastereoisomer of erythro relative configuration [VIA(±); code number: 300868], and
the less mobile product (the more polar)—18.7 g of a white solid with a melting point of 114.5° C.—consisting of the racemic diastereoisomer of threo relative configuration [VIB(±); code number: 300869].

EXAMPLE 5

Resolution of the racemic threo diastereoisomer [VIB(±); code number: 300869] of 3-[4-(3-chlorobenzyloxy) phenyl] 5-(1-hydroxyethyl) oxazolidin-2-one [VI]

11.2 g (0.032 mol) of the pair VIB(±) obtained in Example 4 is added at 0° C. in portionwise to a flask under argon containing 9 g (0.035 mol) of α-methoxy α-trifluoromethylphenylacetyl chloride $\{[\alpha]_D^{20} = -134.6° (C=5.2; CCl_4)\}$ and 30 ml of pyridine. After solubilization with the aid of 25 ml of pyridine, 1.2 g (0.014 mol) of 4-dimethylaminopyridine is added. After 60 hours agitation at ambient temperature, the reaction is complete. The reaction mixture is discharged into 50 ml of water, then extracted 3 times with ether. The organic phase is washed 3 times with 2N HCl, then by a saturated $NaHCO_3$ solution, dried on $MgSO_4$ and evaporated.

The crude mixture obtained is subjected to silica column chromatography under medium pressure (eluant=ethyl acetate-hexane: 50-50) to produce the two separate MOSHER esters VI"B(+) and VI"B(−) in the form of oil:
ester enantiomer VI"B(+) [the more mobile on an $SiO_2$ plate]:
 7.9 g; $[\alpha]_D^{20} = +25.3°$ (C=1.0; $CH_2Cl_2$)
ester enantiomer VI"B(−) [the less mobile on an $SiO_2$ plate]:
 7.6 g; $[\alpha]_D^{20} = -73.7°$ (C=1.1; $CH_2Cl_2$).

4.8 ml of 2N NaOH is added to a solution cooled to −10° C. of 3.6 g (0.0064 mol) of the ester enantiomer VI"B(+) in 50 ml of $CH_3OH$. Saponification is complete after 8 hours of agitation at 20° C. After cold concentration, the reaction medium is diluted with 160 ml of methyl ethyl ketone and 50 ml of ice/water mixture. After decantation, the organic phase is washed with a saturated NaCl solution, dried on $MgSO_4$ and then evaporated. By flash chromatography (eluant=ethyl acetate-hexane: 70-30), 2 g (yield=90%) of a white solid is recovered (m.p.=90° C.) which is the threo enantiomer (+) [VIB(+); code number: 300872] of 3-[4-(3-chlorobenzyloxy) phenyl] 5-(1-hydroxyethyl) oxazolidin-2-one:
$[\alpha]_D^{20} = +39.5°$ (C=1.03; $CH_2Cl_2$)
absolute configuration: (S,S).

Saponification, under the same conditions as above, of the ester enantiomer VI"B(−) leads to the threo enantiomer (−) [VIB(−); code number: 300873] of 3-[4-(3-chlorobenzyloxy) phenyl] 5-(1-hydroxyethyl) oxazolidin-2-one:
melting point: 90° C.
$[\alpha]_D^{20} = -41.5°$ (C=1.01; $CH_2Cl_2$)
absolute configuration: (R,R).

EXAMPLE 6

Resolution of the racemic erythro diastereoisomer [VIA(±); code number: 300868] of 3-[4-(3-chlorobenzyloxy) phenyl] 5-(1-hydroxyethyl) oxazolidin-2-one [VI]

In 30' 6.15 g of the pair VIA(±) obtained in Example 4, dissolved in 30 ml of pyridine, is added to a solution cooled to 0° C. of 4.25 g (0.023 mol) of 2-phenoxy propanoyl chloride $\{[\alpha]_D^{20} = +26.3°$ (C=1.0: $CH_2Cl_2$)$\}$ and 0.65 g (0.00053 mol) of 4-dimethylaminopyridine in 50 ml of pyridine. The esterification reaction is complete after 16 hours of agitation at 20° C. The reaction medium is treated as in the esterification of Example 5. By medium pressure chromatography (eluant=ethyl acetate-hexane: 40-60), there are recovered:

the ester enantiomer VI'A(+) [the more mobile on an $SiO_2$ plate]:

3.51 g; $[\alpha]_D^{20}=+37.6°$ (C=1.0; $CH_2Cl_2$); and the ester enantiomer VI'A(−) [the less mobile on a $SiO_2$ plate]:

3.66 g; $[\alpha]_D^{20}=-14.2°$ (C=1.0; $CH_2Cl_2$).

Saponification by 2N NaOH (1.3 equiv.) of these ester enantiomers for 2 hours at 20° C. under the same operating conditions as in Example 5, followed by conventional ethyl acetate extraction allows isolation respectively of:

the erythro enantiomer (+) [VIA(+); code number: 340177] of 3-[4-(3-chlorobenzyloxy) phenyl] 5-(1-hydroxyethyl) oxazolidin-2-one:

melting point: 78° C.

$[\alpha]_D^{20}=+16.6°$ (C=1.0; $CH_2Cl_2$)

absolute configuration: (S, R); and the erythro enantiomer (−) [VIA(−); code number: 340176] of 3-[4-(3-chlorobenzyloxy) phenyl] 5-(1-hydroxyethyl) oxazolidin-2-one:

melting point: 78° C.

$[\alpha]_D^{20}=-16.2°$ (C=1.0; $CH_2Cl_2$)

absolute configuration: (R, S).

By implementing the processes constituting the above Examples 1 to 6, but starting with the appropriate reagents, the other compounds (VI) are obtained.

In Table 1 below there are shown the physicochemical data of the enantiomers prepared in Examples 5 and 6.

EXAMPLE 7

Preparation of the threo stereoisomer (−) (R,R) mesylate of 3-[4-(3-chlorobenzyloxy) phenyl] 5-(1-hydroxyethyl) oxazolidin-2-one [IXB(−); code number 340270]

7.4 g (5 ml, 65 mmol) of mesyl chloride is poured into a 500 ml flask containing 15 g (43 mmol) of enantiomer code number 300873 prepared in Example 5, in solution in 150 ml of $CH_2Cl_2$. After cooling to −10° C. 6.5 g (9 ml, 65 mmol) of triethylamine is added drop by drop under an argon atmosphere.

After one hour of agitation at ambient temperature, the reaction medium is poured onto an ice/water mixture and extracted 3 times with $CH_2Cl_2$ (150 ml). The organic phases are washed by a saturated $NaHCO_3$ solution (50 ml), then a saturated NaCl solution (2×50 ml).

After drying on $MgSO_4$, filtraton and evaporation under reduced pressure, 18 g of white solid is recovered corresponding to the stereoisomer expected:

melting point: 117° C.

$[\alpha]_D^{20}=-45.2°$ (C=1; $CH_2Cl_2$).

EXAMPLE 8

Preparation of the erythro stereoisomer (−) (R, S) of 3-[4-(3-chlorobenzyloxy) phenyl] 5-(1-dimethylaminoethyl) oxazolidin-2-one [IA(−): code number 200562]

A stainless steel "bomb" containing 8.2 g (19.5 mmol) of the mesylate obtained in Example 7 and 30 ml (≃0.45 mol) of dimethylamine is heated to 100° C.

After 4 hours agitation under a pressure of $4.10^5$ Pa, the reaction medium is concentrated.

The precipitate recovered is purified by flash silica column chromatography (eluant: $CH_2Cl_2$—$CH_3OH$: 96-4).

Thus, 4.2 g of a colourless product corresponding to the expected product is recovered.

EXAMPLE 9

Preparation of the threo enantiomer (−) (R,R) of 3-[4-hydroxyphenyl] 5-(1-hydroxyethyl) oxazolidin-2-one [XIB(−); code number 340315]

39.3 g (0.125 mol) of the enantiomer of code number 300873 prepared in Example 5 is introduced into a 1 liter flask containing 4 g of 10% Pd/C in suspension in 350 ml of 95% ethanol. After 2 hours strong agitation in a hydrogen atmosphere, the hydrogenolysis reaction is complete. The catalyst is recovered by filtration and the filtrate is evaporated under reduced pressure to leave a light yellow oil which crystallises. Stirring for one hour in pentane provides 27 g (yield: 97%) of a white solid corresponding to the product expected:

melting point: 149° C.

$[\alpha]_D^{20}=-73.2°$ (C=1.0; $CH_3OH$).

The other enantiomers of 3-[4-hydroxyphenyl] 5-(1-hydroxyethyl) oxazolidin-2-one are obtained by a similar process from the appropriate reagents and are entered in Table 3 below.

EXAMPLE 10

Preparation of the threo enantiomer (R,R) (−) of 3-[4-(3-methoxybenzyloxy) phenyl] 5-(1-hydroxyethyl) oxazolidin-2-one [I; code number: 200436]

Into a flask surmounted by a condenser are introduced, successively, 1 g (0.0045 mol) of 3-(4-hydroxyphenyl) 5-(1-hydroxyethyl) oxazolidin-2-one [XI] (code number 340315), 15 ml of acetonitrile, 1.2 g (0.0089 mol) of finely ground $K_2CO_3$, 0.1 g of KI and 0.75 ml (0.77 g, 0.005 mol) of 3-methoxy-1-chloromethyl benzene. After 3 hours agitation under reflux, the inorganic substances are separated by filtration on sintered glass and the filtrate is diluted with 150 ml of water. The decanted aqueous phase is extracted with $CH_2Cl_2$ (2×50 ml). The organic phase is washed with a saturated NaCl solution, dried on $MgSO_4$ and filtered, then evaporated. The white solid recovered is purified by flash silica chromatography (eluant: $CH_2Cl_2$—$CH_3OH$: 96-4). After evaporation, 0.93 g of the product expected (crystallized, colourless) is recovered.

Yield: 62% melting point: 116° C.

$[\alpha]_D^{20}=-41.9°$ (C=1; $CH_2Cl_2$)

elementary analysis for $C_{19}H_{21}NO_5$: 342,366

Calc. (%) C 66.46 H 6.16 N 4.08. Found (%) C 66.71 H 6.43 N 4.30.

By implementing the processes exemplified above, but starting with the appropriate reagents, the other compounds (I) are obtained, certain of which are entered in Table 2 below.

TABLE 1

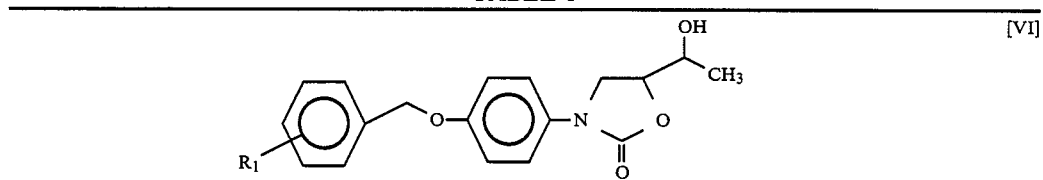

[VI]

| Code Number | $R_1$ | Absolute Configuration | $[\alpha]_d^{20}$ (C = 1; CH$_2$Cl$_2$) | Empirical formula | Molecular weight | Melting point (°C.) | | ELEMENTARY ANALYSIS % | | |
|---|---|---|---|---|---|---|---|---|---|---|
| | | | | | | | | C | H | N |
| 300873 | 3-Cl | (R ,R) | −41.5° | C$_{18}$H$_{18}$ClNO$_4$ | 347.789 | 90 | Cal. | 62.16 | 5.22 | 4.03 |
| | | | | | | | Found | 61.99 | 5.23 | 3.76 |
| 300872 | 3-Cl | (S, S) | +39.5° | C$_{18}$H$_{18}$ClNO$_4$ | 347.789 | 90 | Cal. | 62.16 | 5.22 | 4.03 |
| | | | | | | | Found | 61.99 | 5.28 | 3.88 |
| 340176 | 3-Cl | (R, S) | −16.2° | C$_{18}$H$_{18}$ClNO$_4$ | 347.789 | 78 | Cal. | 62.16 | 5.22 | 4.03 |
| | | | | | | | Found | 61.85 | 5.41 | 3.78 |
| 340177 | 3-Cl | (S, R) | +16.6° | C$_{18}$H$_{18}$ClNO$_4$ | 347.789 | 80 | Cal. | 62.16 | 5.22 | 4.03 |
| | | | | | | | Found | 62.77 | 5.48 | 4.09 |

TABLE 2

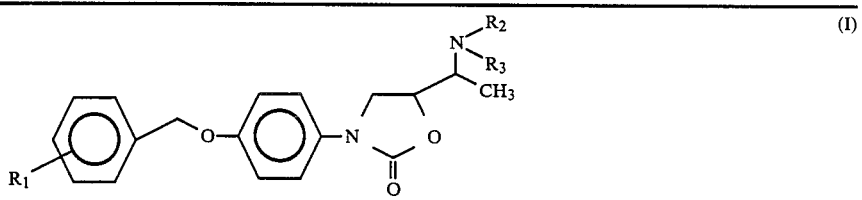

(I)

| Code Number | $R_1$ | $R_2$ | $R_3$ | Configuration | $[\alpha]_D^{20}$ | Empirical formula | Molecular weight | Melting point (°C.) | | ELEMENTARY ANALYSIS % | | |
|---|---|---|---|---|---|---|---|---|---|---|---|---|
| | | | | | | | | | | C | H | N |
| 340271 | 3-Cl | CH$_3$ | H | (R, S) | −66° (C = 1; H$_2$O)$^a$ | C$_{19}$H$_{21}$N$_2$O$_3$Cl | 360.861 | 94$^b$ | Cal. | 57.44 | 5.58 | 7.05$^a$ |
| | | | | | | | | 209$^a$ | Found | 56.85 | 5.32 | 6.97 |
| 340179 | " | CH$_3$ | " | (S, R) | +31.1°(C = 1; CH$_2$Cl$_2$)$^b$ +59.8°(C = 1; CH$_3$OH)$^a$ | C$_{19}$H$_{21}$ClN$_2$O$_3$ | 360.831$^b$ | 91$^b$ 198$^a$ | Cal. Found | 57.44 57.10 | 5.58 5.79 | 7.05$^a$ 7.53 |
| 340276 | " | CH$_3$ | " | (R, R) | −35.4°(C = 0,8; CH$_2$Cl$_2$)$^b$ | C$_{19}$H$_{21}$N$_2$O$_3$Cl | 360.861$^b$ | 220$^a$ | Cal. Found | 57.44 57.20 | 5.58 5.61 | 7.05$^a$ 7.05 |
| 340333 | " | CH$_3$ | " | (S, S) | +44.4°(C = 1; CH$_2$Cl$_2$)$^b$ | C$_{19}$H$_{21}$ClN$_2$O$_3$ | 360.831$^b$ | 85$^b$ 225$^a$ | Cal. Found | 57.44 57.30 | 5.58 5.86 | 7.05$^a$ 7.18 |
| 200562 | 3-Cl | CH$_3$ | CH$_3$ | (R, S) | −34.7°(C = 1; CH$_2$Cl$_2$)$^b$ −29.7°(C = 1; CH$_2$Cl$_2$)$^a$ | C$_{20}$H$_{23}$ClN$_2$O$_3$ C$_{20}$H$_{24}$Cl$_2$N$_2$O$_3$ +2.6% H$_2$O | 374.857 422.302 | 124$^b$ 117$^a$ | Cal. Found | 56.88 56.79 | 6.02 5.84 | 6.63$^a$ 6.53 |
| 340321 | " | H | H | (R, R) | −38.3°(C = 1; CH$_2$Cl$_2$)$^b$ | C$_{18}$H$_{19}$ClN$_2$O$_3$ | 346.805$^b$ | 99 | Cal. Found | 55.10 55.11 | 5.39 5.11 | 7.14$^a$ 7.06 |
| 340366 | " | " | " | (S, S) | +41°(C = 1; CH$_2$Cl$_2$)$^b$ | C$_{18}$H$_{19}$ClN$_2$O$_3$ | 346.805$^b$ | 106$^b$ 220$^a$ | Cal. Found | 56.40 56.13 | 5.26 5.19 | 7.31$^a$ 7.12 |
| 340742 | 3-Cl | CH$_3$ | CH$_3$ | (R*, S*) (±)$^e$ | (±)$^e$ | C$_{20}$H$_{23}$ClN$_2$O$_3$ C$_{20}$H$_{24}$Cl$_2$N$_2$O$_3$ +1.5 H$_2$O | 374.857 438.346 | 114$^b$ 86–90$^a$ | Cal. Found | — — | — — | — — |
| 340743 | 3-OCH$_3$ | CH$_3$ | CH$_3$ | (R*, S*) (±)$^e$ | (±)$^e$ | C$_{21}$H$_{26}$N$_2$O$_4$ C$_{25}$H$_{30}$N$_2$O$_8$ | 370.434 486.506 | oil$^b$ 132$^c$ | Cal. Found | — — | — — | — — |
| 340744 | 3-OCH$_3$ | CH$_3$ | CH$_3$ | (R, S) | −47.5°(C = 0.08;CH$_3$OH)$^b$ −40°(c = 0.1;95%EtOH) | C$_{21}$H$_{26}$N$_2$O$_4$ C$_{25}$H$_{30}$N$_2$O$_8$ | 370.434 486.506 | 62–64$^b$ 126–130$^c$ | Cal. Found | — — | — — | — — |
| 340745 | 3-Cl | H | CH$_3$ | (R*, S*) (±)$^e$ | (±)$^e$ | C$_{19}$H$_{21}$ClN$_2$O$_3$ C$_{19}$H$_{22}$Cl$_2$N$_2$O$_3$ | 360.831 397.296 | 102$^b$ 196$^a$ | Cal. Found | — — | — — | — — |
| 340746 | 3-Cl | CH$_3$ | CH$_3$ | (S, R) | +28°(c = 2;CH$_3$OH)$^b$ +47°(c = 0.6;CH$_3$OH)$^d$ | C$_{20}$H$_{23}$ClN$_2$O$_3$ C$_{24}$H$_{27}$ClN$_2$O$_7$ | 374.857 490.929 | — 150$^d$ | Cal. Found | — — | — — | — — |
| 340747 | 3-OCH$_3$ | CH$_3$ | CH$_3$ | (S, R) | +49°(c = 0.06; 95% EtOH)$^b$ +37°(c = 0.1; 95% EtOH)$^c$ | C$_{21}$H$_{26}$N$_2$O$_4$ C$_{25}$H$_{30}$N$_2$O$_8$ | 370.434 486.506 | 63$^b$ 126$^c$ | Cal. Found | — — | — — | — — |
| 340748 | 3-Cl | CH$_3$ | CH$_3$ | (R*, R*) (±)$^e$ | (±)$^e$ | C$_{20}$H$_{23}$ClN$_2$O$_3$ C$_{20}$H$_{24}$Cl$_2$N$_2$O$_3$ | 374.857 411.324 | 99$^b$ 200$^a$ | Cal. Found | — — | — — | — — |
| 340749 | 3-OCH$_3$ | CH$_3$ | CH$_3$ | (R*, R*) (±)$^e$ | (±)$^e$ | C$_{21}$H$_{26}$N$_2$O$_4$ C$_{21}$H$_{27}$ClN$_2$O$_4$ | 370.434 406.899 | oil$^b$ 220$^a$ | Cal. Found | — — | — — | — — |
| 340750 | 3-Cl | H | H | (R*, S*) (±)$^e$ | (±)$^e$ | C$_{18}$H$_{19}$ClN$_2$O$_3$ C$_{18}$H$_{20}$Cl$_2$N$_2$O$_3$ | 346.805 383.270 | 91$^b$ 231$^a$ | Cal. Found | — — | — — | — — |

TABLE 2-continued

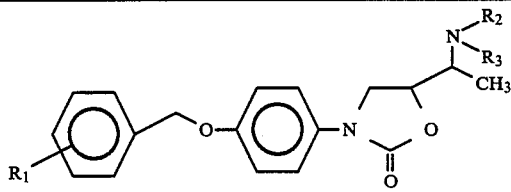

(I)

| Code Number | R₁ | R₂ | R₃ | Configuration [α]$_D^{20}$ (±) | Empirical formula | Molecular weight | Melting point (°C.) | ELEMENTARY ANALYSIS % | C | H | N |
|---|---|---|---|---|---|---|---|---|---|---|---| a = hydrochloride;
b = base;
c = fumarate;
d = maleate;
e = Chemical Abstract nomenclature

TABLE 3

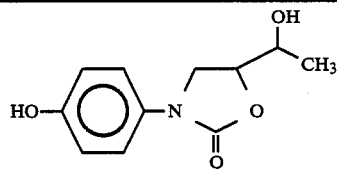

(XI)

| Code Number | Absolute Configuration | [α]$_D^{20}$ (C = 1 ; CH₃OH) | Empirical formula | Molecular weight | Melting point (°C.) | ELEMENTARY ANALYSIS % | C | H | N |
|---|---|---|---|---|---|---|---|---|---|
| 340315 | (R ,R) | −73.2° | C₁₁H₁₃NO₄ | 223.222 | 149 | Cal. | 59.18 | 5.87 | 6.28 |
|  |  |  |  |  |  | Found | 59.42 | 6.11 | 6.13 |
| 200158 | (S, S) | +71.7° | C₁₁H₁₃NO₄ | 223.222 | 154 | Cal. | 59.18 | 5.87 | 6.28 |
|  |  |  |  |  |  | Found | 59.42 | 6.11 | 6.13 |
| 200356 | (R, S) | −28.5° | C₁₁H₁₃NO₄ | 223.222 | 163 | Cal. | 59.18 | 5.87 | 6.28 |
|  |  |  |  |  |  | Found | 58.88 | 5.73 | 6.12 |
| 200357 | (S ,R) | +29.8° | C₁₁H₁₃NO₄ | 223.222 | 163 | Cal. | 59.18 | 5.87 | 6.28 |
|  |  |  |  |  |  | Found | 59.14 | 5.85 | 6.09 |

The compounds according to the invention have been tested on laboratory animals and have exhibited pharmacological activity and especially monoamine oxidase, particularly type B monoamine oxidase, inhibiting activity.

This activity has been given prominence by the implementation of the protocol described by P. DOSTERT et al. in J. Pharm. Parmacol., 1983, 35, 161–165; this protocol is based on enzymatic tests carried out with or without preincubation in particular for 60 minutes and it allows measurement in vitro of the inhibiting effect with regard to the MAO-A and the MAO-B of the brain of a rat.

In Table 4 below are shown the inhibiting concentrations 50 (IC 50) for the A and B forms of MAO, obtained for a number of compounds (I) according to the invention following the above protocol applied to a total rat brain homogenate, with 1 g of tissue/16 ml of phosphate buffer of pH 7.4.

TABLE 4

| Compound tested Code No. | Configuration | IC 50 (A) in nM (Preincubation of 60') | IC 50 (B) in nM | IC 50 (A) / IC 50 (B) |
|---|---|---|---|---|
| 340271$^a$ | (R, S) (−) | 7430 | 78 | 95 |
| 340179$^a$ | (S, R) (+) | 18300 | 1160 | 16 |
| 340276$^a$ | (R, R) (−) | 148000 | 1350 | 110 |
| 340333$^a$ | (S, S) (+) | >100000 | 1280 | >78 |
| 200562$^a$ | (R, S) (−) | >100000 | 53 | >1887 |

TABLE 4-continued

| Compound tested Code No. | Configuration | IC 50 (A) in nM (Preincubation of 60') | IC 50 (B) in nM | IC 50 (A) / IC 50 (B) |
|---|---|---|---|---|
| 340321$^a$ | (R, R) (−) | >100000 | 5340 | >19 |
| 340366$^a$ | (S, S) (+) | >100000 | 1641 | >61 |
| 340742$^a$ | (R*, S*) (±) | >1000000 | 160 | >6250 |
| 340743$^c$ | (R*, S*) (±) | 1000000 | 400 | 2500 |
| 340744$^c$ | (R, S) (−) | >1000000 | 250 | >4000 |
| 340745$^a$ | (R*, S*) (±) | 15000 | 50 | 300 |
| 340746$^d$ | (S, R) (+) | >1000000 | 1600 | >625 |
| 340747$^c$ | (S, R) (+) | >1000000 | 15000 | >67 |
| 340748$^a$ | (R*, R*) (±) | 300000 | 20000 | >15 |
| 340749$^a$ | (R*, R*) (±) | >30000 | 300000 | >10 |
| 340750$^a$ | (R*, S*) (±) | 210000 | 380 | 553 | a = hydrochloride;
c = fumarate;
d = maleate;
Substrate concentrations: [¹⁴C]5-hydroxytryptamine = 480 μM, [¹⁴C]phenylethylamine = 12 μM for the study of the inhibition of forms A and B.

It can be seen from Table 4 that the compounds (I) according to the invention have an MAO inhibiting activity and in particular that the compounds of erythro configuration (R,S) (−) or (R*, S*) (±) are powerful and selective inhibitors of type B MAO.

Furthermore, a subacute 15 day toxicological study carried out on the rat revealed the innocuous nature of the compounds (I) according to the invention and of their pharmaceutically acceptable acid addition salts.

It follows from the foregoing that the compounds (I) of the invention and their pharmaceutically acceptable acid additions salts find therapeutic use, especially as medicaments for inhibiting monoamine oxidase, in particular type B monoamine oxidase. It will therefore be possible to use these compounds and salts for the preparation of a medicament for the treatment of depression, Parkinson's disease and neurological deficiencies especially connected with senescence.

The invention extends to pharmaceutical compositions comprising, as their active principle, at least one compound selected from among the compounds (I) according to the invention and their pharmaceutically acceptable acid addition salts, in association with a pharmaceutically acceptable carrier. These compositions will be administered orally in the form of compressed tablets, lozenges or gelatine-coated pills, for example, with dosages of the active principle ranging up to 50 mg/day in one or more doses, rectally in the form of suppositories containing up to 300 mg of active principle (1 to 2 per day) or indeed in the form of injectable solutions containing up to 300 mg of active principle (1 to 2 injections per day).

We claim:

1. The four individual stereoisomers of a compound of the formula:

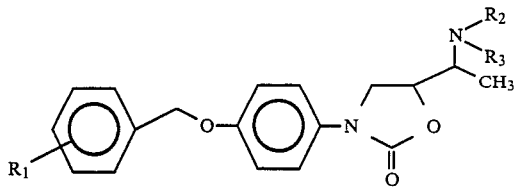

wherein $R_1$ is hydrogen atom, a $C_1$-$C_4$ alkoxy group, a trifluoromethyl group, or one or two halogen atoms; and $R_2$ and $R_3$ are selected from the group consisting of a hydrogen atom and a $C_1$-$C_4$ alkyl group, each of the two pairs of the corresponding racemic diastereoisomers and a mixture of the four stereoisomers, as well as their pharmaceutically acceptable acid addition salts.

2. The stereoisomers, pairs and mixture of claim 1, in which $R_1$ is chlorine atom or a methoxy group in the meta position and $R_2$ and $R_3$ are a hydrogen atom or a methyl group.

3. The stereoisomers and pairs of claim 1 of erythro (−) relative configuration.

4. The stereoisomers of claim 3, of absolute configuration (R, S).

5. A pharmaceutical composition comprising a stereoisomer, a pair or the mixture of claim 1 or their pharmaceutically acceptable acid salts and a pharmaceutically acceptable carrier.

6. The four individual stereoisomers of a compound of the formula:

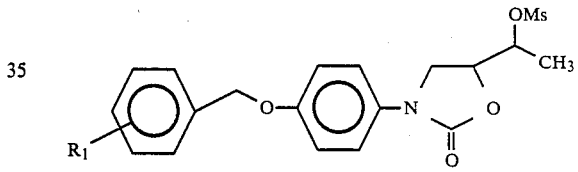

wherein Ms is a mesyl group and $R_1$ is a hydrogen atom, a $C_1$-$C_4$ alkoxy group, a trifluoromethyl group or one or two halogen atoms.

* * * * *